United States Patent [19]

Hauck

[11] Patent Number: 5,074,303
[45] Date of Patent: Dec. 24, 1991

[54] RATE ADAPTIVE CARDIAC PACER INCORPORATING SWITCHED CAPACITOR FILTER WITH CUTOFF FREQUENCY DETERMINED BY HEART RATE

[75] Inventor: John A. Hauck, Shoreview, Minn.

[73] Assignee: Cardiac Pacemakers, Inc., St. Paul, Minn.

[21] Appl. No.: 490,459

[22] Filed: Mar. 8, 1990

[51] Int. Cl.$^5$ .............................. A61N 1/365
[52] U.S. Cl. .................. 128/419 PG; 128/671
[58] Field of Search ............. 128/419 PG, 671, 670, 128/901

[56] References Cited

U.S. PATENT DOCUMENTS

| | | | |
|---|---|---|---|
| 4,381,786 | 5/1983 | Duggan | 128/419 PG |
| 4,665,919 | 5/1987 | Mensink et al. | 128/419 PG |
| 4,686,987 | 8/1987 | Salo et al. | 128/419 PG |
| 4,722,351 | 2/1988 | Phillipps et al. | 128/696 |
| 4,733,667 | 3/1988 | Olive et al. | 128/419 PG |
| 4,913,145 | 4/1990 | Stotts | 128/419 PG |

Primary Examiner—William E. Kamm
Assistant Examiner—Kennedy J. Schaetzle
Attorney, Agent, or Firm—Haugen and Nikolai

[57] ABSTRACT

A rate adaptive cardiac pacemaker incorporating a switched capacitor filter whose cut-off frequency is varied as a function of heart rate allows respiration-related signals appearing in the intracardiac impedance waveform to be separated from signals relating to systolic events over a frequency range of interest, allowing either or both of the respiration-related signal component or the systolic event component to be used in adjusting the pacing rate.

6 Claims, 1 Drawing Sheet

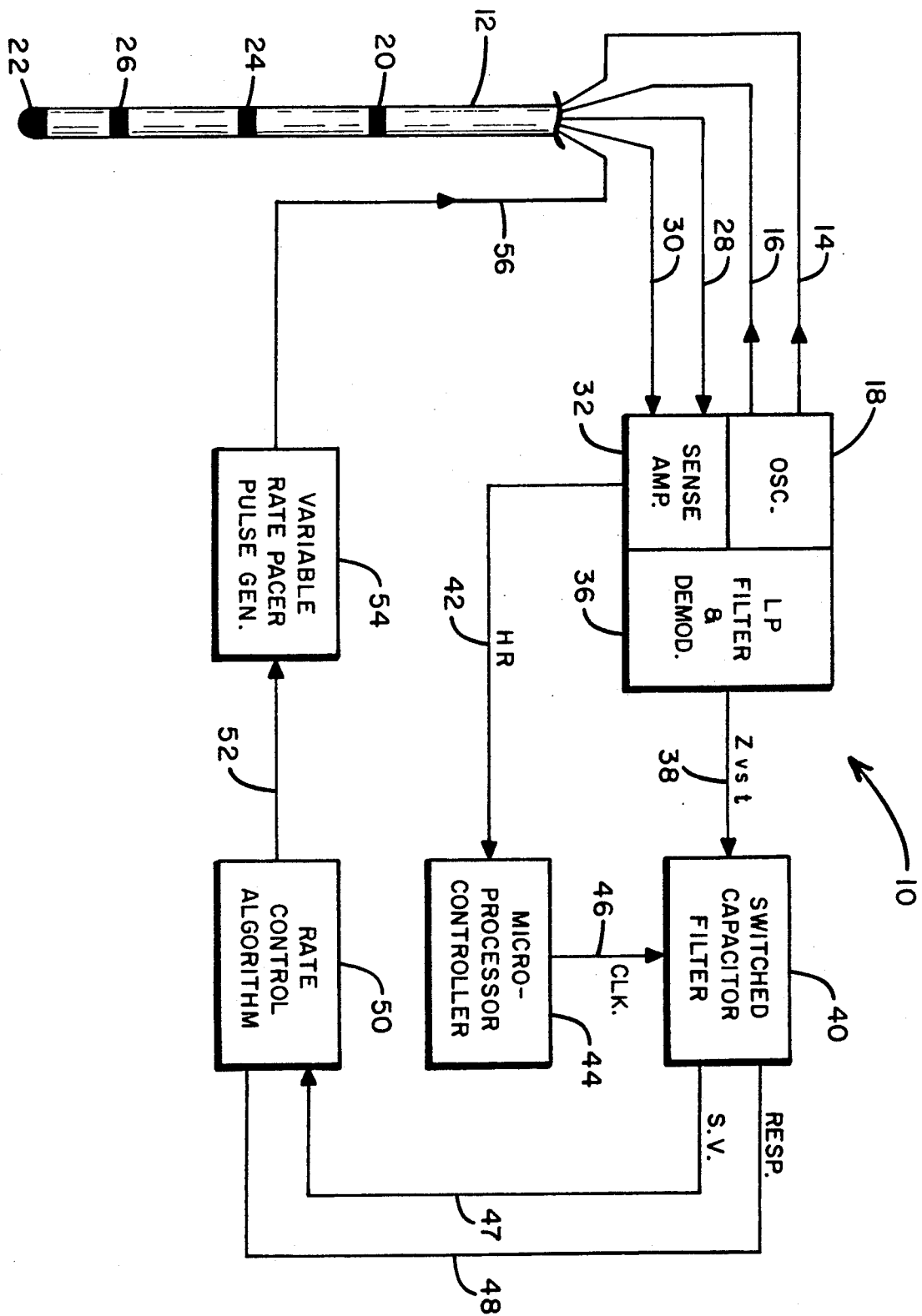

RATE ADAPTIVE CARDIAC PACER INCORPORATING SWITCHED CAPACITOR FILTER WITH CUTOFF FREQUENCY DETERMINED BY HEART RATE

BACKGROUND OF THE INVENTION

I. Field of the Invention

This invention relates generally to implantable cardiac pacing apparatus, and more particularly to a demand pacemaker whose pacing rate is determined by physiologic need as determined by changes in stroke volume and/or respiration rate and respiration depth measured using impedance plethysmography techniques.

II. Discussion of the Prior Art

As is set forth in the "Discussion of Prior Art" of the Brian D. Pederson, et al patent application Ser. No. 07/490,392, filed 3-8-90, and entitled "Adaptive Pacemaker Utilizing Respiration Related Variation in Cardiac Chamber Volume or Pressure as a Controlling Parameter" which is being filed concurrently herewith and which is assigned to applicants' assignee, there are a relatively large number of rate adaptive pacemaker designs disclosed in the patent art in which various physiologic parameters are measured and used to adapt the pacing rate of an implantable cardiac pacer to a patient's metabolic need. The invention of the aforereferenced application, discloses the design of a rate adaptive pacemaker in which signal components present in a measured impedance waveform related to intrathoracic volume and pressure variations are used in developing a control signal for the rate adaptive pacer. That is to say, volume or pressure variations within the right ventricle or right atrial chamber attributable to respiratory activity is sensed and signal processed to derive a rate controlling signal for the pacer. In that arrangement, by utilizing a low-pass filter, higher frequency components attributable to systolic events can be discriminated against in favor of the low frequency component attributable to respiratory activity. However, because there is considerable spectral overlap of the systolic event signal and the respiration signal over the range of normal physiologic conditions, it becomes difficult to separate the two utilizing a fixed cut-off linear filter. For example, in the case of intracardiac impedance measurements where respiration is the signal of interest, if a fixed 3 dB cut-off frequency (fo) of 0.25 Hz (low-pass) is employed, the fundamental of the respiration wave will pass when the patient is at rest. However, during exercise, the breathing rate fundamental frequency can approach or exceed 60 breaths-per-minute (1 Hz) and if a filter with a fixed cut-off characteristic is being employed, the respiration component, i.e., the signal of interest, will be attenuated along with the systolic component.

It is accordingly a principal object of the present invention to provide an improved signal processing circuit for processing an intracardiac or intrathoracic impedance signal capable of separating components due to respiratory activity from components due to systolic events over a wide range of physiologic conditions.

Another object of the invention is to provide a signal processing circuit for a rate adaptive pacer in which an adaptive filter is employed, allowing the cut-off frequency of the filter to be varied as a function of heart rate.

SUMMARY OF THE INVENTION

The foregoing objects of the invention are achieved in accordance herewith by providing a rate adaptive pacemaker incorporating means for sensing intracardiac impedance variations and producing a time varying voltage signal in accordance therewith. This voltage signal is applied as an input to a switched capacitor adaptive filter whose cut-off frequency is nominally set to discriminate between respiratory events and systolic events found in the impedance waveform when the patient is at rest. Further means are provided for measuring the patient's heart rate and then using the heart rate as a clock input for the adaptive filter whereby the cut-off frequency thereof shifts upwards as heart rate increases and downwards as heart rate again drops. In this way, the respiratory and systolic events can be separated and independently utilized in creating the overall control signal for adjusting the pacing rate of the implanted pacemaker.

DESCRIPTION OF THE DRAWING

The foregoing features, objects and advantages of the invention will become apparent to those skilled in the art from the following detailed description of a preferred embodiment, especially when considered in conjunction with the accompanying drawing which illustrates by means of a electrical block diagram a preferred embodiment of the invention.

DESCRIPTION OF THE PREFERRED EMBODIMENT

Referring to the drawing, there is indicated generally by numeral 10 a rate adaptive pacer in which one, the other or both of respiration and stroke volume are utilized in developing a rate control signal for a variable rate pacer pulse generator whereby the pacing rate is made to vary with changes in metabolic need or demand. In the Salo et al U.S. Pat. No. 4,686,987 which is assigned to applicant's assignee, a rate adaptive cardiac pacer is described in which means are provided for measuring stroke volume by utilizing an intracardiac impedance waveform and deriving stroke volume-related information from the peak-to-peak swings in the measured impedance waveform. As is described in that patent, an endocardial lead or catheter 12 is routed through the vascular system such that its distal end portion is positioned within the right ventricle. Conductors 14 and 16 couple the output of a carrier oscillator 18 to a pair of drive electrodes 20 and 22 mounted on the surface of the catheter 12. Disposed between the drive electrodes 20 and 22 are a pair of sense electrodes 24 and 26 which are coupled by conductors 28 and 30 to the inputs of a sensing amplifier 32. The output of the sense amplifier is delivered to an impedance waveform generator 36 which may include amplifying, filtering and demodulating circuitry like that disclosed in the above-referenced Salo et al U.S. Pat. No. 4,686,987.

When the catheter 12 has its drive and sense electrodes disposed in the heart's right ventricle and an alternating current signal from the high frequency oscillator 18 is impressed across the drive electrodes 20 and 22, that high frequency signal will be modulated by the changes in impedance of the blood between electrodes 24 and 26. Thus, the signal appearing at the output point 38 from the impedance waveform generator 36 is a time-varying signal corresponding to the impedance (Z) measured within the heart.

The Z vs. t signal appearing on line 38 is applied to a switched capacitor filter 40, various forms of which are known in the art. Important to the present embodiment of the invention is the fact that the frequency filter functions can be tuned by a clock, allowing the filter's cut-off frequency to be shifted by an externally-applied control signal. In this regard, the sense amplifier 32 outputs a signal corresponding to a patient's heart rate on line 42 which is applied as an input to a microprocessor controller 44. The microprocessor controller functions to generate clock signals on line 46 corresponding to an N-beat average. It can be seen, then, that the cut-off frequency of the filter 40 is made to shift as a function of the patient's heart rate.

Where stroke volume is the parameter of interest to be separated from the Z vs. t impedance waveform, a high-pass switched capacitor filter is used, where the cut-off frequency is set to effectively attenuate lower frequency components due to respiration. As the respiration rate increases during physical exercise so as to approach the frequency of systolic events, the cut-off frequency of the filter 40 also shifts upwards because of the heart rate-related clock signal applied thereto via conductor 46. Hence, the filter continues to discriminate against the lower frequency respiratory artifacts.

As mentioned earlier, where it is desired to separate out the respiration signal from the Z vs. t waveform, a low-pass implementation for the switched capacitor filter 40 would be chosen, permitting the respiration signal to pass through the filter 40 and appear on line 48 uncontaminated by the stroke volume signal. It is also possible with classical filter design methods as applied to switched capacitor technology to implement filter 40 as a state-variable device such that both the stroke volume component and the respiration signal component can be made to appear on the separate output lines 47 and 48.

As in the Brian D. Pederson, et al application filed concurrently herewith, either or both of the respiration signal and the stroke volume signal from the switched capacitor filter 40 may be used in accordance with a rate control algorithm 50 to produce a rate control signal on line 52 which, when applied to the variable rate pacer pulse generator 54, changes the rate at which heart stimulating pulses are conveyed over the conductor 56 to the stimulating tip electrode 22 on the distal end of the lead 12. In this fashion, the variable rate pacer pulse generator 54 can be made to track metabolic need.

It can be seen then that the present invention provides a way in which a patient's average heart rate can be used as a dynamic control parameter for setting the cut-off frequency of a switched capacitor filter allowing better separation of signal components in the impedance waveform due to systolic events from those components occasioned by ventilation. Although the preferred embodiment is described using a switched capacitor filter, it is possible to implement an adaptive filter that performs as the one described, by switching in one of a plurality of resistors in a filter topology so as to adjust the corner frequency. It is intended that the scope of this invention cover the use of any adaptive linear filter using heart rate as the control parameter and the corner or center frequency, fo, as the operand.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. In a rate adaptive pacer of the type comprising an implantable variable rate pulse generator operative to produce electrical stimulating pulses at a predetermined lower rate with the patient at rest, endocardial lead means coupled to said pulse generator having a stimulating electrode for applying said stimulating pulses to heart tissue and further electrodes for sensing an electrical impedance signal within at least one cardiac chamber, and signal processing means coupled to said further electrodes for producing a rate control signal for said pulse generator relating to said impedance signal, the improvement comprising:
   (a) adaptive filter means in said signal processing means, said adaptive filter means having a variable cut-off characteristic automatically determined by a changeable physiologic parameter;
   (b) means coupled to said lead means for automatically producing a cut-off frequency control signal in relation to changes in said physiologic parameter; and
   (c) means for applying said cut-off frequency control signal to said adaptive filter means for automatically changing the cut-off characteristic of said filter means with changes in said physiologic parameter.

2. In a rate adaptive pacer of the type comprising an implantable variable rate pulse generator operative to produce electrical stimulating pulses at a predetermined lower rate with the patient at rest, endocardial lead means coupled to said pulse generator having a stimulating electrode for applying said stimulating pulses to heart tissue and further electrodes for sensing an electrical impedance signal within at least one cardiac chamber, said electrical impedance signal being modulated by systolic events and ventilatory events and signal processing means coupled to said further electrodes for producing a rate control signal for said pulse generator relating to said impedance signal, the improvement comprising:
   (a) switched capacitor filter means in said signal processing means, said filter means having a cut-off characteristic determined by the rate at which clock pulses are applied to said filter means;
   (b) means coupled to said lead means for producing said clock pulses in relation to the heart rate of the patient; and
   (c) means for separating the impedance signal into a first component modulated by systolic events and a second component modulated by ventilatory events wherein said means for separating comprises means for applying said clock pulses to said filter means for changing the cut-off characteristic of said filter means with changes in heart rate.

3. The adaptive rate pacer as in claim 2 wherein said means for producing clock pulses comprises microprocessor means coupled to said further electrodes and programmed to compute a heart rate value which is an average over a predetermined number of beats and produce said clock pulses at a frequency relating to the average heart rate.

4. The adaptive rate pacer as in claim 2 wherein said switched capacitor filter means is a low-pass filter.

5. The adaptive rate pacer as in claim 2 wherein said switched capacitor filter means is a high-pass filter.

6. The adaptive rate pacer as in claim 2 wherein said switched capacitor filter means is a state variable device.

* * * * *